United States Patent [19]

Pomplun et al.

[11] Patent Number: 4,663,106

[45] Date of Patent: May 5, 1987

[54] FORMATION OF ELASTICIZED PORTIONS OF DISPOSABLE GARMENTS AND OTHER ARTICLES

[75] Inventors: William S. Pomplun; Robert L. Popp, both of Winnebago County; Paul A. Woon, Outagamie County; Carl G. Schroth, Outagamie County; Robert A. Stevens, Outagamie County, all of Wis.

[73] Assignee: Kimberly-Clark Corporation, Neenah, Wis.

[21] Appl. No.: 768,176

[22] Filed: Aug. 22, 1985

Related U.S. Application Data

[63] Continuation of Ser. No. 605,968, May 1, 1984, abandoned.

[51] Int. Cl.$^4$ .............................................. B29C 61/02
[52] U.S. Cl. .............................. 264/230; 264/342 RE; 156/85; 156/160; 98/40.27
[58] Field of Search .............................. 156/84–86, 156/160, 164, 229, 264–265, 269, 297, 299, 497, 499, 301; 98/40.27; 34/225, 233, 34; 264/230, 342 RE

[56] References Cited

U.S. PATENT DOCUMENTS

| 2,685,246 | 8/1954 | Saunders | 98/40.27 |
|---|---|---|---|
| 2,849,347 | 8/1958 | Uziel | 156/82 |
| 3,075,868 | 1/1963 | Long | 156/82 |
| 3,210,227 | 10/1965 | Shichman | 156/82 |
| 3,320,868 | 5/1967 | Apouchtine | 98/40.27 |
| 3,322,584 | 5/1967 | Welin-Berger | 156/82 |
| 3,575,782 | 4/1971 | Hansen. | |
| 3,639,917 | 2/1972 | Althouse. | |
| 3,644,159 | 2/1972 | Edkvist | 156/82 |
| 3,819,401 | 6/1974 | Massengale. | |
| 3,847,183 | 11/1974 | Meyer. | |
| 3,912,565 | 10/1975 | Koch et al. . | |
| 3,955,577 | 5/1976 | Gellert et al. | 604/366 |
| 4,014,724 | 3/1977 | Rausing | 264/230 |
| 4,092,382 | 5/1978 | Heckman | 264/230 |
| 4,110,138 | 8/1978 | Nomara. | |
| 4,172,873 | 10/1979 | Spicer | 264/230 |
| 4,300,967 | 11/1981 | Sigl. | |
| 4,315,791 | 2/1982 | Ishii et al. . | |
| 4,329,315 | 5/1982 | Brower | 264/230 |
| 4,543,154 | 9/1985 | Reiter | 156/301 |
| 4,545,832 | 10/1985 | Hoffmann | 156/86 |

FOREIGN PATENT DOCUMENTS 2467675 5/1981 France .
2016262 9/1979 United Kingdom .

Primary Examiner—David Simmons
Assistant Examiner—Merrell C. Cashion
Attorney, Agent, or Firm—Paul Yee

[57] ABSTRACT

Apparatus and method for forming an elasticized portion of an article having a thermally-elasticizable strip along a marginal portion in which heated air is directed towards the strip at at least two different angles relative to the plane of the strip and at a velocity sufficient to cause oscillation of the marginal portion bearing the thermally-elasticizable strip; these conditions are maintained for a dwell time long enough to render the strip elastic when cooled to ambient conditions.

15 Claims, 17 Drawing Figures

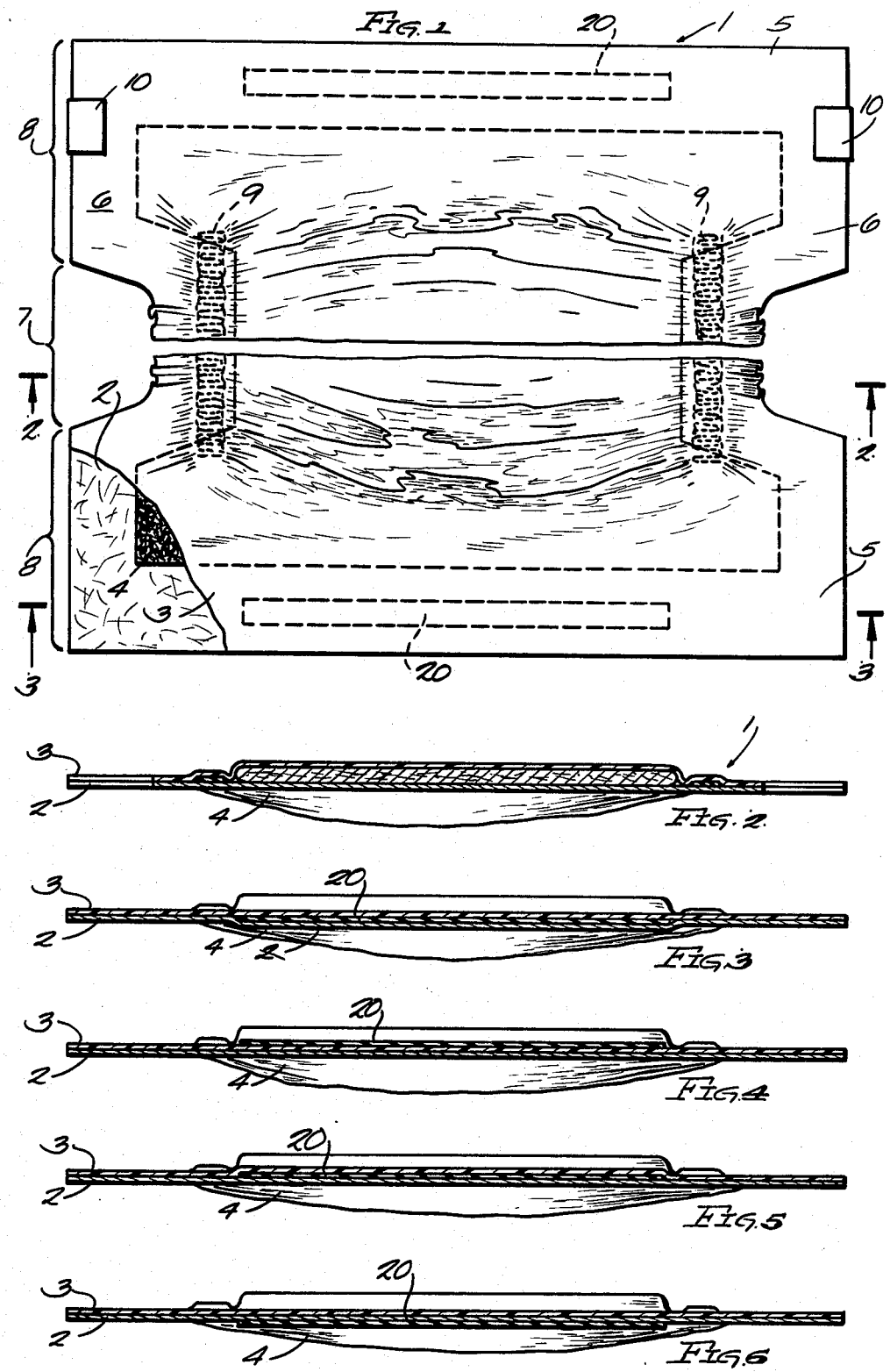

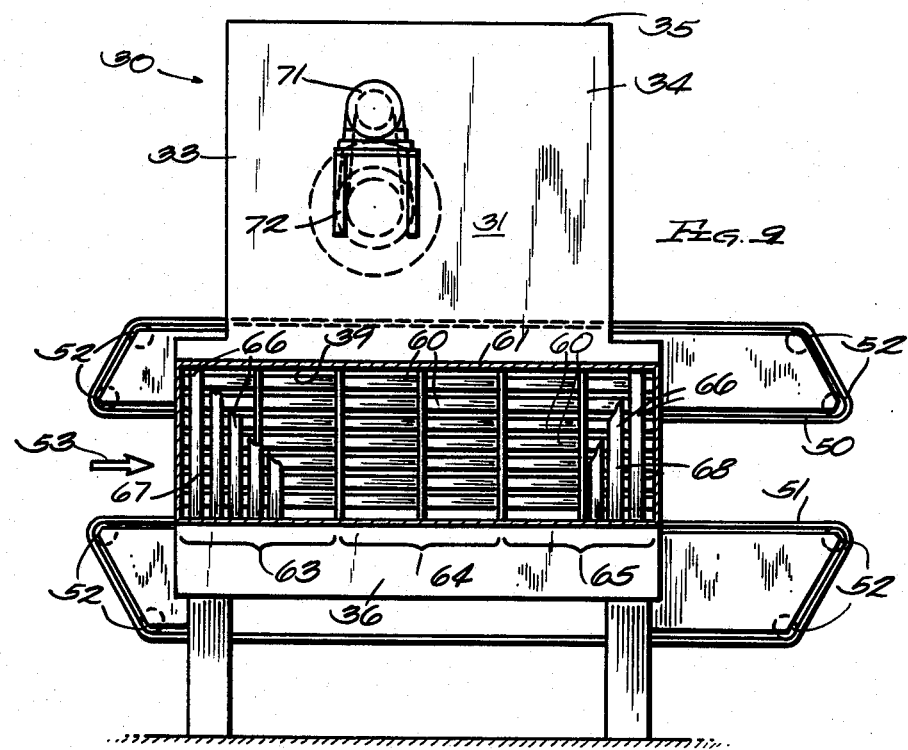
FIG. 9
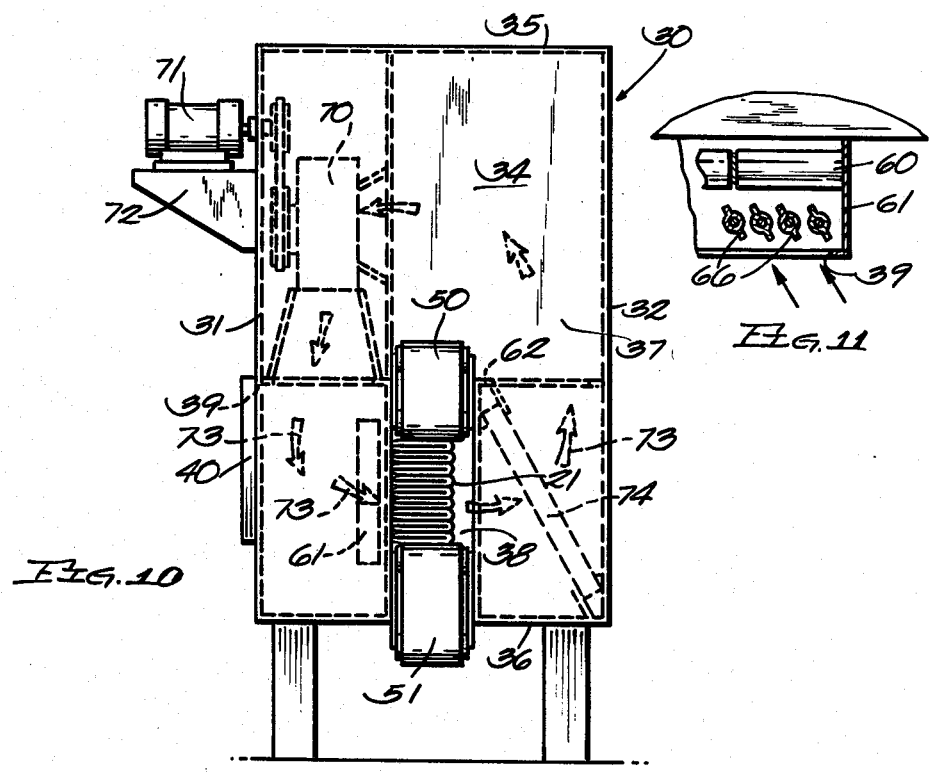
FIG. 10
FIG. 11

FORMATION OF ELASTICIZED PORTIONS OF DISPOSABLE GARMENTS AND OTHER ARTICLES

This is a continuation of application Ser. No. 605,968 filed on May 1, 1984, now abandoned.

TECHNICAL FIELD

This invention relates generally to methods and apparatus for the formation of gathered elasticized portions of articles, typically an elasticized body-encircling portion of a disposable garment.

BACKGROUND

Numerous articles have become commercially important in recent years which are designed for single use or temporary use, and are meant to be disposed of after being used once instead of being laundered or cleaned for re-use. Examples of garments of this general type are disposable diapers; adult incontinence garments; disposable bed sheets; disposable shower caps; garments intended for single use in hospitals such as surgical gowns, surgical hats and booties; and single use or disposable pajamas and the like intended to be worn by patients in a hospital for a short stay. Articles other than garments are also within this type, such as protective covers, dust covers, etc. Single use or disposable articles of this type are made of lightweight film or sheet materials such as thermoplastic films, nonwoven fabrics of various materials such as thermoplastic or cellulosic fibers, paper, coated film or paper, and various composites of one or more of these types of materials. These materials are distinguishable from textiles used to make a sewn garment or article which is intended for long term use and subject to repeated laundering or dry cleaning.

Disposable articles of the type under consideration are economically feasible only when they can be manufactured at high production rates using techniques typical of converting film materials, such as heat sealing, sonic sealing, adhesive bonding, etc., instead of the sewing techniques customary with textile garments meant for long term use. Even with the disposable articles, however, it is often desirable to form an elasticized portion in order to provide a snug fit. In the case of disposable garments intended to be worn by human beings, for example, it may be necessary to provide a gown or similar item with elasticized wrists, or to produce a disposable diaper with elasticized waist portions and leg portions in order to provide a snug fit, or provide disposable booties with an elasticized ankle encircling portion. In the case of other products such as bed sheets and dust covers, a marginal portion that can fit snugly about an article is often required.

Because articles of this type need to be made at high production speeds, the formation of an elasticized portion by sewing in a strip of elastic material as is common in the production of textile garments is not practical. Among the methods that have been developed or proposed in the art to form elasticized portions of disposable products are several which involve the use of heat, such as (1) constructing the article of an oriented thermoplastic film and contact heating selected portions thereof to cause them to heatshrink and form integral elastic portions, see U.S. Pat. No. 3,245,407; (2) application of a tape to the article that is elastic at room temperature but rendered inelastic at elevated temperatures and heating selected portions of the tape to kill its elasticity therein, see U.S. Pat. No. 4,300,967 and published United Kingdom patent application No. 2,016,262; and (3) application of a tape of a material that is inelastic at room temperature but rendered elastic by the application of heat, see U.S. Pat. Nos. 3,639,917 and 3,912,565. The present invention is related to this latter class of processing techniques.

The method disclosure of U.S. Pat. No. 3,639,917 involves heating a garment section bearing heat recoverable elastomeric tape to temperatures in the range of 75° C. to 150° C. such as by use of a hot air gun, iron or an oven. U.S. Pat. No. 3,912,565 discloses forming an elasticized article by heating heatshrinkable uniaxially oriented polyurethane tape to a temperature slightly above its second order phase transition temperature, 100° C. being disclosed as an operable temperature; for this purpose, the patent states the heat may be applied by gas, such as hot air, or liquid. We have now developed new techniques relating to heating thermally-elasticizable material with hot air to render it elastic, but which differs from the methods disclosed in these two patents in the manner in which the hot air is manipulated with respect to direction and velocity of flow; it is believed these differences are advantageous in the manufacture of single or temporary use articles.

DISCLOSURE OF THE INVENTION

Our new process for forming an elasticized marginal portion of an article is briefly described as follows. A strip of thermally-elasticizable material is attached to the article along the marginal portion that is to be elasticized, the material of the strip being of the type that is substantially inelastic at room temperature but is rendered elastic upon thermal activation and remains elastic when cooled back to room temperature. Heated air is directed against the strip to cause it to become elastic. In accordance with our invention: (1) the heated air is directed against the strip at an angle to the plane of the strip, (2) the heated air is directed at least at a first angle to the plane of the strip and a second angle to the plane of the strip, the first and second angles being oppositely inclined to the plane of the strip, and (3) the heated air is at a velocity sufficient to cause the marginal portion of the article bearing the strip to oscillate. We have also developed an apparatus suitable for the practice of the foregoing method which includes an oven having wall portions defining a chamber, an entrance thereto and an exit therefrom; means for circulating heated air through the chamber; means for conveying articles through the chamber arranged with their marginal portions bearing thermally-elasticizable strips in a free or unrestrained condition; and means for directing heated air against the marginal portions bearing the strips at least at a first angle to the plane of each strip and a second angle to the plane of each strip, the first and second angles being oppositely inclined to the plane of each strip. The method and apparatus of this invention provide new and useful results, as explained in detail hereinafter.

DESCRIPTION OF THE DRAWINGS

The present invention is described below, as required by 35 USC §112, in sufficient detail to enable those skilled in the art to practice the invention and to set forth the presently-contemplated best modes for its practice, all by reference to the following drawings in which:

FIG. 1 is a plan view, with portions broken away, of an infant's disposable diaper as an example of a type of article with which the present invention may be practiced;

FIG. 2 is a sectional view of the diaper of FIG. 1 taken along the plane of line 2—2;

FIG. 3 is a sectional view of the diaper of FIG. 1 taken along the plane of line 3—3;

FIG. 4 is a sectional view the same as FIG. 3 illustrating a second structure of the diaper of FIG. 1 suitable for the practice of this invention;

FIG. 5 is a sectional view the same as FIG. 3 illustrating a third structure of the diaper of FIG. 1 suitable for the practice of this invention;

FIG. 6 is a sectional view the same as FIG. 3 illustrating a fourth structure of the diaper of FIG. 1 suitable for the practice of this invention;

FIG. 9 is a side view, with portions broken away, of an apparatus of the present invention;

FIG. 10 is an end view of the apparatus of FIG. 9;

FIG. 11 is a horizontal sectional view of a portion of the apparatus of FIG. 9;

Figure 7A:
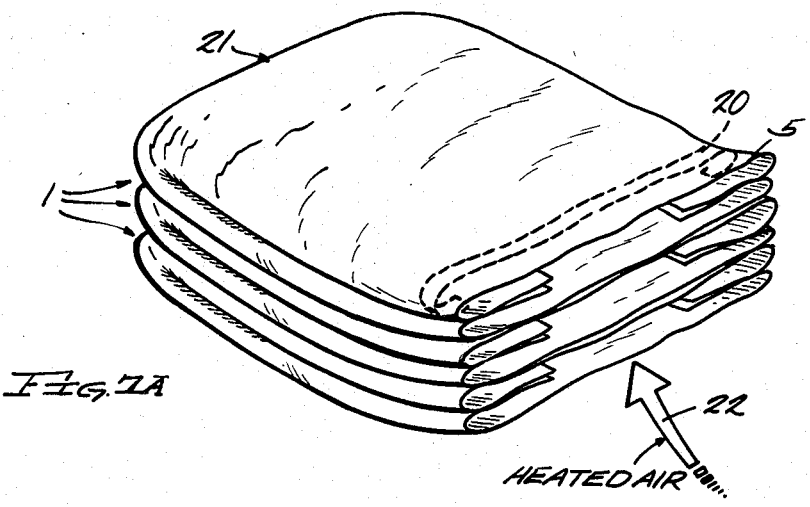
FIGS. 7A, 7B and 7C are perspective views illustrating sequential stages in the processing of a stack of diapers of FIG. 1 according to the method of this invention.

Best Modes for Carrying Out the Invention

The drawings depict the method and apparatus of this invention employed in the formation of elasticized waist portions of a disposable infant's diaper, which is a particularly useful application of the present invention. However, it should be borne in mind that this invention can be practiced advantageously with numerous other types of articles and that the diaper is described herein in an exemplary, not limiting, sense.

The detailed description is divided into four parts: (a) a background discussion, (b) a method description, (c) an apparatus description, and (d) a description of operational conditions.

(a) Background

FIGS. 1, 2 and 3 illustrate a disposable diaper 1 comprising a liquid-permeable inner liner 2, a liquid-impermeable outer layer 3, and an absorbent batt 4 secured therebetween. The inner liner 2 and outer layer 3 are larger than the absorbent batt 4 and have end marginal portions 5 extending beyond the ends of the batt and side marginal portions 6 extending beyond the sides of the batt. The liner 2 and outer layer 3 are secured to each other along the marginal portions 5 and 6. Conventional materials are used for these elements of the diaper 1. The inner liner 2 may be any soft, flexible porous sheet which passes fluids therethrough and may comprise a nonwoven web or sheet of polyolefin fibers such as polypropylene, wet strength tissue paper, a spun woven filament sheet, etc. It may be treated with a surfactant to aid in liquid transfer. The outer layer 3 is a liquid-impermeable layer and may comprise a thin web or sheet of plastic film such as polyethylene, polypropylene, polyvinyl chloride or the like; it may be transparent or have an embossed or matte surface to be opaque. The absorbent batt 4 may be of any suitable material, generally cellulosic material such as an air-formed batt of wood pulp fibers commonly known as "fluff".

The inner liner 2, outer layer 3 and batt 4 may be combined with one another in any suitable manner to form the finished diaper. The elements may be bonded to one another by means of strips or patterns of hot melt or pressure sensitive adhesive, overall or patterned heat sealing, strips of double faced pressure sensitive adhesive tape, etc. A particularly effective bonding system is the use of spaced parallel lines of hot melt adhesive on the interior surface of the outer layer 3, with the absorbent batt bonded to the layer 3 along sections of the lines of adhesive and the inner liner 2 bonded to the layer 3 along other sections of the lines of adhesive within the marginal portions 5 and 6 outside the batt.

The diaper is of a generally hourglass or I shape including a central narrowed crotch section 7 and waist band sections 8 along each end thereof. Elongate elastic means 9 are secured in place adjacent the absorbent batt 4 on each side thereof to develop gathered elastic leg portions that are conformable with an infant's legs. Conventional pressure sensitive tapes 10 are attached to one waist band section 7. The diaper 1 is fitted to an infant with the inner layer 2 against the child's skin; one marginal portion 5 encircles part of the infant's waist and the other marginal portion 5 encircles the balance, with the two being overlapped and joined together by the pressure sensitive adhesive tapes 10 in order to hold the diaper in place.

The structure of diaper 1 as described to this point forms no part of the present invention, and further details of its construction may be had by reference, for example, to U.S. Pat. No. 4,050,462.

(b) Method Description

For the purposes of the present invention, the diaper 1 of FIGS. 1-3 includes thermally-elasticizable strips 20 which are secured to the interior surface of the outer layer 3, best seen in FIG. 3, there being one strip 20 positioned within each end marginal portion 5 spaced inwardly from the outer edge thereof. The strips 20 have a selected width and selected length, about ¼" to 1" wide being suitable for most articles and the length being as long as required for the particular article to which the strips are applied. A strip 20 usually will be relatively thin, approximately 0.75 to 3 mils being suitable in most instances. As used in this description and the claims, the term "plane" of a strip 20 refers to the area bounded by its length and width.

FIGS. 4-6 show alternate positions for the strips 20 which also are suitable: the exterior surface of the outer layer 3 (FIG. 4), the interior surface of the liner 2 (FIG. 5), and the exterior surface of the liner 2 (FIG. 6).

A thermally-elasticizable strip 20 may be secured to the liner 2 or outer layer 3 by any suitable means, but most usefully by pressure sensitive adhesive on the surface of the strip 20 which is to contact the outer liner or outer layer. The pressure sensitive adhesive may be physically disposed on such surface in the form of one or more spaced parallel lines of adhesive extending longitudinally of the strip 20, or as a ribbon, layer or pattern of adhesive on such surface of the element. The adhesive may be any pressure sensitive adhesive appropriate to the type of materials employed for the strip 20 and the layer to which it is to be secured, such as a hot melt pressure sensitive adhesive.

The thermally-elasticizable strip 20 is to be made of a material that is relatively inelastic at room or ambient temperature but which is capable of being rendered elastic when heated to an elevated temperature, and remaining elastic when cooled back to room temperature. Thus, a strip 20 is to be made of a thermally-activated elastic material, i.e. a material that becomes elastic upon thermal activation. As used in this description and the claims, the term "elastic" is defined to mean that a strip 20 can be manually elongated to at least about 50% of its original length and will return to its original length upon release of the force causing the elongation.

One type of material suitable for the thermally-elasticizable strip 20 is that available from Minnesota Mining and Manufacturing Company identified as its product PSL-GT02900, consisting of several layers of nonwoven fabric surrounding elastomeric threads contained between the layers under 70 to 95% elongation and cemented in place with an acrylic binder material. When heated to the proper temperature, the binder softens sufficiently to allow the elastomeric threads to retract and function as elastomers when the material is cooled to room temperature. Another type of material suitable for the thermally-elasticizable strip 20 is a coextruded film having an inner layer of a polyether block amide resin consisting of linear regular chains of rigid polyamide segments and flexible polyether segments, such as produced from the commercially-available Pebax (Trademark) resins sold by ATO CHEM, and outer layers of ethylene-vinyl acetate copolymer. This type of material is substantially inelastic at room temperature, becomes elastic when heated to an elevated temperature, and remains elastic when cooled to room temperature. Thermally-elasticizable material of this second type is more fully described in the co-pending U.S. patent application Ser. No. 606,182, filed May 1, 1984, entitled Heat-Shrinkable Elastomer, Method of Producing the Elastomer and Articles Utilizing the Elastomer, assigned to the assignee of this application, the disclosure of which is incorporated herein by reference. Both of these types of thermally-elasticizable material are rendered elastic when heated to a temperature range of about 150° F. to 220° F., preferably in the range of about 180° F. to 200° F., and retain their elasticity when cooled back to room temperature subsequent to the heating.

Figure 7B:
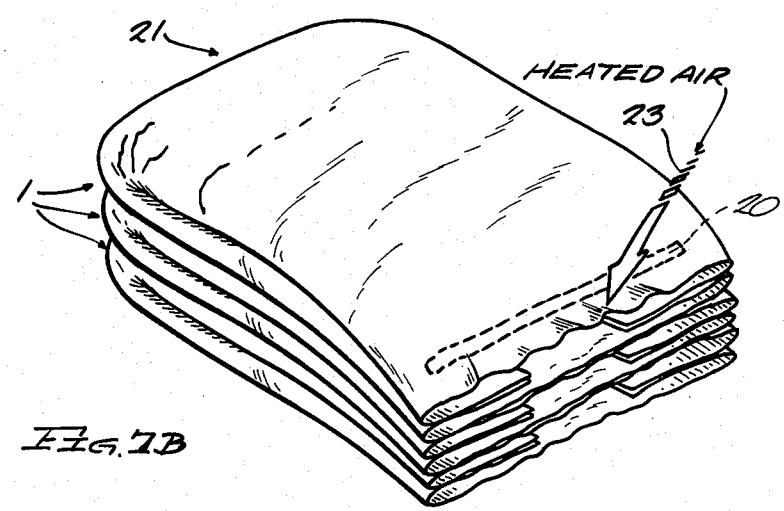
Figure 7C:
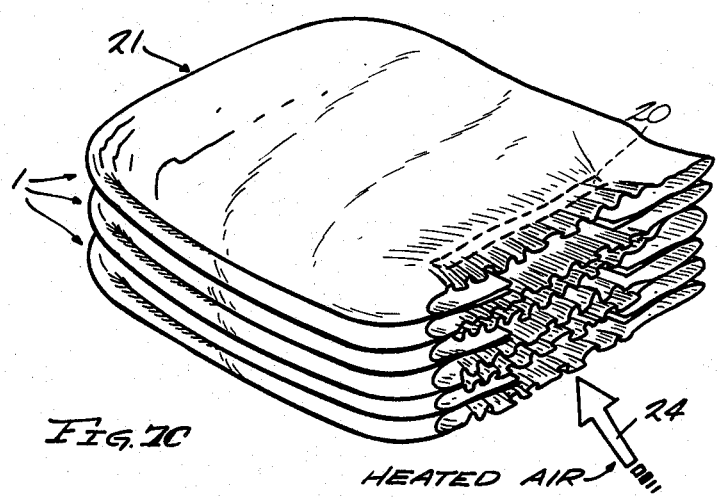

FIGS. 7A, 7B and 7C illustrate the processing of diapers 1 in accordance with the method of this invention.

Diapers 1 are folded longitudinally and then folded in half transversely to a rather narrow width; as shown, it is useful to fold the diapers sufficiently narrow that the strips 20 bend around the folded side portions of the diapers. The diapers when thusly folded have their end marginal portions 5 along which the strips 20 are secured positioned one above the other. It is useful to form a stack 21 of a number of folded diapers having their marginal portions 5 aligned relative to one another in order to increase production rates, but the articles may also be processed one at a time if so desired.

For the practice of this invention, heated air is to be directed against the marginal portions 5; as would be expected, the air is heated to a temperature sufficient to activate the thermally-elasticizable strips 20, i.e. cause them to become elastic, but low enough in temperature to preclude thermal damage to the layers of the diapers to which the elements are secured. However, in accordance with this invention, the heated air is to have three essential characteristics:

(1) The heated air is directed against the marginal portions 5 at an angle to the plane of each strip 20; thus, if the elements 20 are positioned in a horizontal plane, the heated air is to be directed at an angle to the horizontal.

(2) The direction of the heated air is alternated between a first angle to the plane of each strip 20 and a second angle to the plane of each strip 20, the first and second angles being at opposite inclinations to the plane of each strip 20.

(3) The heated air is to have a velocity sufficient to cause the marginal portions 5 to oscillate or flutter. Oscillation as used herein is defined as meaning periodic or cyclic movement of the marginal portions 5 bearing the strips 20; for example, oscillation will result in the marginal portions moving up and down when they are arranged horizontally or side-to-side if arranged vertically. Also, the angle of the heated air defined herein as in (1) and (2) above relative to the plane of a strip 20 refers to the angular relationships determined when the marginal portions are at rest, not when they are oscillating.

FIGS. 7A, 7B and 7C schematically illustrate the foregoing characteristics. Referring first to FIG. 7A, heated air as indicated by the arrow 22 is directed at the end marginal portions 5 of the stack 21 of diapers at a first angle which is inclined upwardly relative to the plane of each strip 20. Next, as shown in FIG. 7B the heated air is directed towards the end marginal portions 5 of the stack 21 of diapers at a second angle shown by arrow 23 which is inclined downwardly relative to the plane of each strip 20. As shown in FIG. 7C, the heated air is directed towards the end marginal portions 5 of the stack of diapers at a third angle depicted by arrow 24, which is the same as the first angle of FIG. 7A.

Processing of the stack 21 of diapers in the foregoing manner can be accomplished by transporting the diapers past three heated air streams directed at the appropriate angles, or by holding the stack of diapers in a fixed position and moving a single heated air stream through the several angles. Further, while the heated air stream is illustrated at being directed at three angles in FIGS. 7A–C, the present invention may be practiced by directing the heated air stream at only the first and second angles of FIGS. 7A and 7B, each inclined at appropriate angles to the plane of the strips 20.

Figure 8:
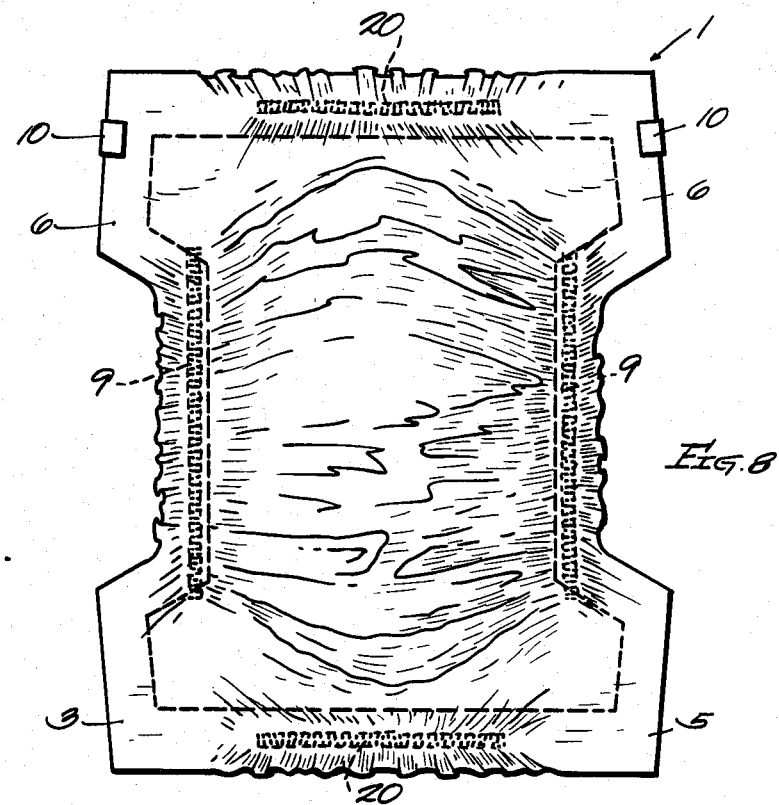
FIG. 8 is a plan view of a diaper of FIG. 1 after processing with the method of this invention.
Figure 12:
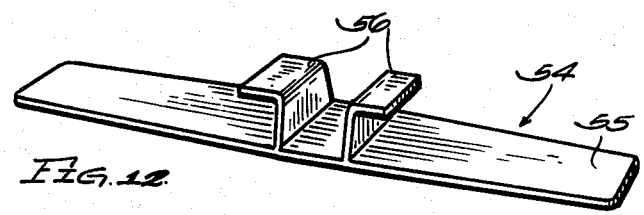
FIG. 12 is a perspective view of an element of the conveyors employed in the apparatus illustrated in FIG. 9.

FIGS. 7A–C illustrate the effect of moving the stack 21 of diapers past three heated air streams directed as described above. In FIG. 7A, the heated air is beginning to heat the end marginal portions 5 along which the thermally-elasticizable strips 20 are secured. As the stack 21 is moved past another heated air stream at the second angle as shown in FIG. 7B, the strips start to be rendered elastic, and thereby begin to contract, under the action of the heated air stream. Finally, see FIG. 7C, as the stack 21 is moved past a third air stream again directed at the first angle towards the strips 20, the strips 20 have been rendered fully elastic and have contracted sufficiently that the free edge portions of the diapers has been gathered as shown in the drawings. Throughout the movement of the stack 21 of diapers through the stages illustrated in FIGS. 7A–C, the heated air is at a velocity sufficient to cause the marginal portions 5 to flutter or oscillate as the diapers are transported past the three streams of heated air. Following the stage of FIG. 7C, the stack 21 of diapers is cooled back to ambient or room temperature. A finished diaper after being processed through the stages of FIGS. 7A-C and cooled is illustrated in FIG. 8. The strips 20 retain their elastic characteristic so that when a diaper is wrapped about an infant, the waist-encircling marginal portions 5 will provide a snug fit.

(c) Apparatus Description

FIGS. 9-13 illustrate an apparatus of this invention which is particularly useful for practicing the method described in part (b).

Referring first to FIGS. 9 and 10, the apparatus comprises an oven indicated by the general reference numeral 30 including: front wall 31, rear wall 32, end walls 33 and 34, top wall 35 and bottom wall 36, all joined as shown to define a chamber 37 within which heated air may be circulated. The end walls 33 and 34 include aligned openings 38, the opening 38 in end wall 34 being shown in FIG. 10. The front wall 31 includes an opening 39 extending across the entire length of the front wall, which is covered by access doors 40 (FIG. 10).

An upper conveyor 50 and lower conveyor 51 are trained about rollers 52 and are each driven by appropriate drive mechanisms, not shown. The lower reach of the upper conveyor 50 enters the chamber 37 of the oven in the direction of arrow 53 through the opening 38 in the end wall 33 and exits the oven through the opening 38 in the end wall 34. The upper reach of the conveyor 50 returns through a top section of the oven as illustrated in the drawings. The upper reach of the lower conveyor 51 enters the oven through opening 38 in the end wall 33 and exits the oven through opening 38 in the end wall 34; its lower reach may extend outside of the oven as shown in the drawings. The conveyors 50 and 51 are made up of a plurality of links 54 of the type illustrated in FIG. 12. Each link 54 has a planer surface 55 and a pair of spaced flanges 56 extending therefrom. The links 54 are connected to a roller chain, not shown, along the flanges 56, and the roller chain is driven to move the conveyors. The links 54 of each conveyor are positioned closely to one another.

Inside the chamber 37 of the oven, a plurality of horizontal louvers 60 are supported in a frame 61 (see FIG. 11) which is secured between the bottom wall 36 of the oven and a cross-panel 62. The horizontal louvers are positioned closely adjacent one side of the conveyors 50 and 51 within the chamber 31. As best seen in FIG. 9, the horizontal louvers 60 are arranged in three banks 63, 64 and 65, each bank including two sets of louvers. The horizontal louvers 60 are pivotally supported in the frame 61 so that each louver may be angularly adjusted individually. The horizontal louvers 60 extend entirely across the opening 39 in the front wall of the oven as shown in FIG. 9.

A plurality of spaced vertical louvers 66 are located within the chamber 31, positioned outboard of the horizontal louvers 60. The vertical louvers 66 also are pivotally supported in the frame 61, and extend entirely across the opening 39 in the front wall of the oven. The vertical louvers 66 are arranged in banks of three, a portion of the first bank 67 located near the end wall 33 and a portion of the third bank 68 located near the end wall 34 being illustrated in FIG. 9.

Air, which may be heated by any suitable means not shown fueled by gas, oil or electricity, is circulated through the chamber 37 of the oven 30 by a fan 70. The fan 70 is located in the chamber 37 near an upper section thereof and driven by a motor 71 supported on a bracket 72 attached to the exterior of the front wall 31 of the oven. As best illustrated in FIG. 10, the fan 70 is arranged to circulate heated air in the manner shown by the arrows 73, through the vertical louvers 66 and horizontal louvers 60 and thence between the upper conveyor 50 and lower conveyor 51, following which the air passes through filters 74 and is returned to the upper section of the oven for recirculation by the fan 70.

Figure 13A:
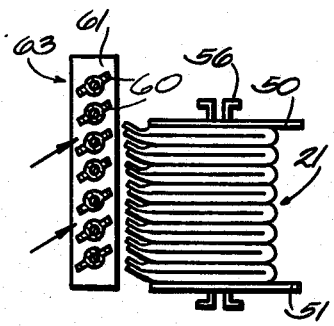
FIGS. 13A, 13B and 13C are schematic views illustrating stages in the sequence of a stack of diapers transversing the apparatus of FIG. 9.
Figure 13B:
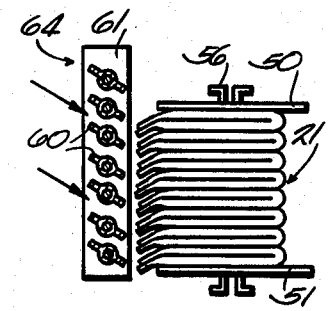
Figure 13C:
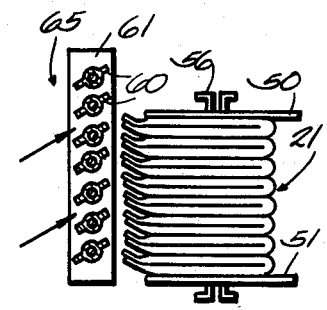

In order to process diapers according to the method of this invention, a stack 21 of diapers 1 is placed between the upper conveyor 50 and lower conveyor 51 in the manner depicted in FIG. 10. The links 54 of each conveyor grip and cover a substantial portion of the upper and lower diapers in the stack since their planar elements 55 have substantial length and width. The stack 21 is arranged between the two conveyors in such fashion that the end marginal portions 5 of each diaper extend beyond or project from the links of the conveyors. The horizontal louvers 60 of the first bank 63 are pivoted within the frame 61 so as to direct heated air at a first angle to the plane of each of the strips 20 secured to the marginal portions 5, as illustrated in FIG. 13A. The horizontal louvers 60 of the second bank 64 are pivoted to direct heated air towards the diapers at a second angle inclined downwardly to the plane of each of the strips 20 as illustrated in FIG. 13B; lastly, the horizontal louvers 60 in the third bank 65 are pivoted in the frame 61 so as to direct air at a third angle in the manner illustrated in FIG. 13C. Thus the horizontal louvers 60 are employed as means for directing the heated air towards the diapers in the manner described previously with respect to FIGS. 7A-C; in this connection, it will be noted the angular direction of the heated air in FIGS. 13A-C correspond to FIGS. 7A-C respectively. The stack 21 of diapers enters the chamber 37 of the oven at the entrance defined by the opening 38 in end wall 33, is transported through the chamber when the conveyors are driven, subjected to heated air which is directed against the thermally elasticizable strips 20 in the described manner so as to activate the elements 20 and render them elastic, and leaves the chamber through the exit defined by opening 38 in end wall 34. The diapers may then be delivered to another transport conveyor, not shown, for final packaging, storage or such other purpose as may be desired.

The vertical louvers 66 are employed for another purpose and their use in the oven 30 is optional. Because there are openings 38 in the end walls 33 and 34 of the oven in order to allow stacks of diapers to be transported through the oven for treatment of the thermally elasticized strips 20, it may be desirable in some instances to include the vertical louvers 66 in order to achieve better heat balance and heat transfer within the oven. The vertical louvers of the first bank 67 thereof may be angled inwardly relative to the chamber 31 of the oven so as to aid in directing the heated air into the oven and reduce the loss of hot air through the opening 38 in end wall 33; similarly, the vertical louvers 66 of the third bank 68 thereof may also be directed inwardly such as shown in FIG. 11 to reduce the loss of hot air through the opening 38 in the end wall 34. The vertical louvers in the middle bank, not shown, normally are pivoted to be perpendicular to the horizontal louvers 60.

(d) Operational Conditions

During the development of this invention as described above, it was determined that the air to be directed towards thermally-elasticizable strips in order to render them elastic should generally be at a temperature in the range of about 150° F. to 220° F., although temperatures outside this range can be used depending on the material used for the strips. This temperature range for the heated air has been found sufficient to render the types of thermally-elasticizable materials described above elastic, and yet not cause thermal damage to either layer of the diapers, which were the articles employed in the developmental work. Heated air at a velocity in the range of about 1,000 to 5,000 feet per minute, preferably about 2,000 to 4,000 feet per minute, is effective to cause oscillation of the marginal portions bearing the thermally-elasticizable strips, and we have found it useful to operate at an air velocity of about 2000 feet per minute. With respect to the angular direction of the heated air relative to the plane of the thermally-elasticizable strip or strips, the heated air should be directed at an angle of about 30 to 60 degrees above and below the plane of a strip; particularly good results have been obtained when the angle of the heated air was inclined approximately 45° to 60° to the plane of a strip. Finally, the articles bearing the thermally-elasticizable strips are subjected to heated air of the foregoing parameters for a dwell time sufficient to render the tape elastic; for this purpose, a dwell time in the range of 2 to 30 seconds is generally enough time for continuing the application of heated air to the articles to cause the thermally-elasticizable strips to contract and form an elasticized marginal portion of an article.

The control or manipulation of the direction of flow and velocity of heated air which forms the central feature of the present invention has several effects which provide an effective technique for producing elasticized marginal portions of articles. First, directing the heated air in the described manner serves to better expose the oscillating marginal portions of the articles to the heated air and opens up more of the area of the thermally-elasticizable strips to the heated air. This results in efficient heat transfer for elasticizing the strips and effective penetration of heat. Secondly, the mechanical action of the oscillating marginal portions bearing the strips results in a slight physical breakdown of the layers to which the strips are attached. This has the effect of reducing the resistance of these layers to the contraction of the strip elements, thereby also permitting more rapid elasticization of the strips. Thirdly, the efficient heat penetration or heat transfer achieved by the present technique slightly softens construction adhesive which may be used to join together the inner liner and outer layer of a diaper article, for example, and to soften adhesive employed to attach the thermally-elasticizable strips to the articles. This feature also has an advantageous effect on the efficiency of the process and facilitates rapid elasticization of the strips. All of these features are of particular importance when a stack of articles is to be treated at a time, such as the stack of diapers referred to above. Heated air when directed in the described manner towards the aligned or stacked marginal portions bearing the thermally-elasticizable strips has proved to be effective in reaching the marginal portions of the inner diapers of articles of the stack. This is important in order to obtain uniform treatment of all articles in a stack, and is of further importance in permitting high production rates.

For these reasons, it is believed that a new and useful method for forming elasticized marginal portions of articles has been described. The description has been developed by reference to certain specific examples of the process and apparatus of this invention, it being understood that these are disclosed by way of example and that those skilled in the relevant art will be able to devise modifications thereto that will remain within the scope of the present invention.

We claim:

1. A method for forming an elasticized marginal portion of an article including the steps of:
   (1) transporting an article along a transport direction, said article having a thermally-elasticizable strip, which defines a predetermined plane and is secured along a marginal portion of the article;
   (2) directing heated air towards the strip with a plurality of louvers, the heated air being at a temperature sufficient to thermally activate the strip to render it elastic, wherein:
     (a) the heated air is directed toward the strip angularly with respect to the plane of the strip,
     (b) the heated air is directed at a first angle with respect to the plane of the strip by supporting a first set of said louvers at a first louver angle,
     (c) the heated air is directed at a second angle with respect to the plane of the strip by supporting a second set of said louvers at a second louver angle,
     (d) said first and second louver angles have opposite inclinations with respect to the plane of the strip,
     (e) said second louver set is located along the transport direction at a position side by side with said first louver set, and
     (f) the heated air has a velocity sufficient to cause oscillation of the marginal portion of the article to which the strip is secured; and
   (3) continuting the application of the heated air to the article for a sufficient time to render the strip elastic and cause it to contract and form an elasticized marginal portion of the article.

2. A method according to claim 1, wherein: the heated air is directed towards the strip at first and second angles of about 30 to 60 degrees to the plane of the strip.

3. A method according to claim 1, wherein: the heated air directed towards the strip is at a temperature in the range of about 150° F. to 220° F.

4. A method according to claim 1, wherein: the heated air directed towards the strip is at a velocity in the range of about 1,000 to 4,000 feet per minute.

5. A method according to claim 1, wherein: the heated air is directed towards the strip at first and second angles in the range of 30 to 60 degrees to the plane of the strip, a temperature in the range of about 150° F. to 220° F., and a velocity of about 1,000 to 4000 feet per minute.

6. A method according to claim 1, 2, 3, 4, or 5, wherein: a plurality of articles each having a thermally-elasticizable strip secured along a marginal portion thereof are arranged in a stack, with said marginal portions of each article being aligned relative to one another and in an unrestrained condition, and the heated air is directed towards said marginal portions to cause oscillation thereof.

7. A method according to claim 1, 2, 3, 4 or 5, wherein the oscillation of the marginal portion of the article to which the strip is secured reduces the resistance of the marginal portion to the contraction of the elasticizable strip.

8. A method according to claim 1, 2, 3, 4 or 5, wherein the heated air directed toward the strip at said first angle moves the marginal portion of the article in a first direction and the heated air directed toward the strip at said second angle moves the marginal portion of the article in a second direction to thereby open up more of the area of the strips to the heated air and allow an effective penetration of heat thereto.

9. A method as recited in claim 1, wherein said directing step (2) directs heated air with a plurality of louvers comprised of three banks of adjustable louvers, the first bank adjusted to direct heated air at said first angle relative to the plane of said strip, the second bank adjusted to direct heated air at said second angle relative to the plane of said strip, and the third bank located side by side with the second louver bank and adjusted to direct heated air at a third angle relative to the plane of said strip.

10. A method as recited in claim 1, wherein said providing step (1) provides said article within said chamber with a first conveyor and a second conveyor which have a stack of said articles located therebetween.

11. A method for forming an elasticized marginal portion of an article including the steps of:
    (1) providing an article having a thermally-elasticizable strip which defines a predetermined plane and is secured along a marginal portion of the article;
    (2) transporting said article along a transport direction through a heating chamber having an exit portion and an entrance portion;
    (3) directing heated air towards the strip with a first and a second set of louvers located within said chamber, the heated air being at a temperature sufficient to thermally activate the strip to render it elastic, wherein:
    (a) the heated air is directed toward the strip angularly with respect to the plane of the strip,
    (b) the heated air is directed at a first angle to the plane of the strip by supporting said first set of louvers at a first louver angle;
    (c) the heated air is directed at a second angle to the plane of the strip by supporting said second set of louvers at a second louver angle;
    (d) said first and second louver angles have opposite inclinations with respect to the plane of the strip,
    (e) said second louver set is located along the transport direction at a position side by side with said first louver set, and
    (f) the heated air has a velocity sufficient to cause oscillation of the marginal portion of the article to which the strip is secured;
    (4) continuing the application of the heated air to the article for a sufficient time to render the strip elastic and cause it to contract and form an elasticized marginal portion of the article; and
    (5) adjusting a third set of louvers located at said chamber entrance portion and a fourth set of louvers located at said chamber exit portion to direct heated air inwardly relative to said chamber entrance and exit portions.

12. A method according to claim 11, wherein:
the heated air is directed towards the strip at first and second angles of about 30 to 60 degrees to the pane of the strip.

13. A method according to claim 11, wherein:
the heated air directed towards the strip is at a temperature in the range of about 150° F. to 220° F.

14. A method according to claim 11, wherein:
the heated air directed towards the strip is at a velocity in the range of about, 1,000 to 4,000 feet per minute.

15. A method according to claim 11, wherein:
the heated air is directed towards the strip at first and second angles in the range of 30 to 60 degrees to the plane of the strip, a temperature in the range of about 150° F. to 220° F., and a velocity of about 1,000 to 4,000 feet per minute.

* * * * *